United States Patent [19]

Burke

[11] Patent Number: 5,962,732
[45] Date of Patent: Oct. 5, 1999

[54] PROCESS FOR THE PREPARATION OF 3-PENTENOIC ACID FROM BUTADIENE USING A NICKEL CATALYST

[75] Inventor: Patrick Michael Burke, Wilmington, Del.

[73] Assignees: E. I. du Pont de Nemours and Company, Wilmington, Del.; DSM N.V., Galeen, Netherlands

[21] Appl. No.: 09/213,207

[22] Filed: Dec. 17, 1998

[51] Int. Cl.⁶ .................................................. C07C 51/14
[52] U.S. Cl. ............................................ 562/522; 562/521
[58] Field of Search .................................... 562/521, 522

[56] References Cited

U.S. PATENT DOCUMENTS

| | | | |
|---|---|---|---|
| 4,894,474 | 1/1990 | Maerkl et al. | 560/206 |
| 4,925,972 | 5/1990 | Maerkl et al. | 560/106 |
| 5,145,995 | 9/1992 | Burke | 562/522 |
| 5,250,726 | 10/1993 | Burke | 562/522 |
| 5,618,983 | 4/1997 | Burke | 568/454 |
| 5,672,732 | 9/1997 | Agterberg et al. | 560/207 |

OTHER PUBLICATIONS

Fell (Fette, Seifen, Anstrichm.; 76(5); 193–6), 1974.

*Primary Examiner*—Porfirio Nazario-Gonzalez
*Assistant Examiner*—Robert W. Deemie

[57] ABSTRACT

Process for making 3-pentenoic acid by reacting butadiene with carbon monoxide in the presence of nickel and an iodide source.

6 Claims, No Drawings

PROCESS FOR THE PREPARATION OF 3-PENTENOIC ACID FROM BUTADIENE USING A NICKEL CATALYST

BACKGROUND OF THE INVENTION

3-Pentenoic acid is a well-known intermediate which can be used to make both caprolactam for nylon 6 and adipic acid for nylon 6,6.

The use of cobalt to catalyze the conversion of butadiene to 3-pentenoic acid is known. This reaction requires the presence of a base, such as pyridine, and relatively high pressures, e.g., 3,000 to 10,000 psig and temperatures, e.g., 130° C. to 160° C. See U.S. Pat. Nos. 4,925,972 and 4,894,474.

The use of rhodium and palladium to catalyze the conversion of butadiene to 3-pentenoic acid is also known. See U.S. Pat. Nos. 5,494,041; 5,250,726; 5,145,995 and 5,672,732. The use of these metals suffers from the disadvantages of the high cost of the metals and the use of relatively high temperatures, i.e., above 140° C.

BRIEF SUMMARY OF THE INVENTION

The present invention is a process for preparing 3-pentenoic acid by reacting butadiene and carbon monoxide in a solvent containing a carboxylic acid in the presence of a source of nickel, a source of iodide, optionally water, and optionally a promoter at a temperature between about 60° C. and about 140° C. and a pressure between about 200 psig and about 4000 psig.

DETAILED DESCRIPTION

In the process of the present invention, butadiene is reacted with carbon monoxide in the presence of a source of nickel and HI or selected metal iodides in a carboxylic acid-containing solvent. The reaction can be carried out at temperatures in the range of about 60° C. to about 140° C. and pressures in the range of about 200 psig to about 4000 psig. The nickel and iodide combination is believed to act as a catalyst for the reaction. The process may be carried out in the presence of water and/or in the presence of a promoter.

The nickel portion of the catalyst may be finely divided nickel metal (alone or on a support such as carbon or alumina) or a nickel compound which is or becomes soluble in the reaction medium. Suitable nickel compounds include nickel(II) salts such as nickel acetate or nickel iodide, nickel(0) compounds such as $Ni(COD)_2$ [COD=cyclooctadiene] or $Ni(CO)_2(P(C_6H_5)_3)_2$. The nickel catalyst should be used at a concentration between about 20 and about 200 mmoles/liter of reaction medium. The butadiene conversion rate becomes too slow at lower concentrations of nickel. Higher concentrations of nickel are limited by solubility.

The iodide portion of the catalyst may be HI or any metallic iodide which is capable of generating HI under the reaction conditions. Iodides of the following metals are suitable: B, Al, Ga, Sc, Y, La, Ce, Pr, Nd, Sm, Eu, Gd, Tb, Dy, Ho, Er, Yb, Lu, Ge, Sn, Ti, Zr, Cr, Mo, W, Mn, Fe, Co, Ni and Zn. Highly ionic iodides such as NaI and LiI are not suitable.

The reaction may be promoted further with the use of various promoters. The reaction is strongly promoted by nitrogen bases and their iodide salts, for example lutidinium iodide, tetrabutylammonium iodide, methyltriphenylphosphonium iodide. The base strength (pKa) of the base is not critical provided there is an excess of HI over base under the reaction conditions. Bases varying in strength from simple alkylamines and imidazoles to alkyl-substituted ureas and thioureas promote the reaction.

Suitable organic nitrogen bases include pyridine, optionally substituted with $C_1$–$C_5$ alkyl or $C_6$–$C_{20}$ aryl groups. Substituted pyridines such as the isomeric lutidines and even the highly hindered 2,6-di-t-butylpyridine are particularly effective. Polymeric pyridines such as poly(vinylpyridine) may also be used.

Other suitable organic nitrogen bases include quinoline, optionally substituted with alkyl or aryl groups; isoquinoline, optionally substituted with alkyl or aryl groups; imidazole, optionally substituted with alkyl or aryl groups; thiazole, optionally substituted with alkyl or aryl groups; and oxazole, optionally substituted with alkyl or aryl groups. In the above compounds, preferred alkyl substitutents are $C_1$–$C_5$ alkyl groups and preferred aryl substitutents are $C_6$–$C_{20}$ aryl groups, such as phenyl, substituted phenyl, naphthyl, and phenanthryl.

The promoter may also be the hydrogen iodide salt or a quaternary iodide salt of the above organic nitrogen bases. For example, 2,6-lutidinium iodide and 1,3-dimethylimidazolium iodide are effective promoters in the presence of excess hydrogen iodide.

Other suitable organic nitrogen base promoters are alkyl-substituted ureas and thioureas, and aliphatic amides such as N,N-dimethylacetamide.

The promoter may also be an alkyl, aryl or aryl-alkyl phosphine. The term "alkyl" demotes $C_1$ to $C_8$ straight or branched groups. The term "aryl" denotes phenyl, substituted phenyls (especially $C_1$–$C_5$ alkyl substituted phenyls), and condensed aromatics such as naphthyl and phenanthryl. The phosphines may be monodentate or bidentate. If a bidentate phosphine is used, it is preferred that it be of the formula $R^3_2P$-Q-$PR^4_2$ in which Q is a 3 to 6 carbon atom bridging group and $R^3$ and $R^4$ are the same or different $C_1$–$C_{10}$ alkyl or $C_6$–$C_{20}$ aryl groups. Example of suitable bidentate ligands may be found in U.S. Pat. No. 5,618,983.

Compounds of Group VI metals (Cr, Mo, W) may also be used as promoters. Suitable promoters include molybdenum hexacarbonyl, molybdenum(II) acetate dimer, and molybdenum (III) halide, where the halide is chlorine, bromide, or iodide. Preferred is $Mo(CO)_6$, which strongly promotes butadiene carbonylation with Ni/HI, Ni/AlI$_3$ and Ni/CrI$_3$ catalysts.

Preferred reaction conditions are those in which the ratio of iodide to nickel is in the range of 2/1 to 20/1, the ratio of nitrogen base or phosphine to nickel is in the range 2/1 to 20/1. The preferred ratio of iodide to promoter depends on the base strength of the promoter. For pyridine bases and for phosphines, this ratio should be greater than one; for weaker nitrogen bases such as tetramethylurea, the ratio of iodide to promoter is preferably less than one.

It is preferred to carry out the reaction in the presence of water, which speeds up the reaction and gives a higher yield of 3-pentenoic acid. It is important, however, to limit the amount of water, because too high concentrations can slow the reaction down. Preferred water concentration is in the range of about 1.5% to about 6.0% by weight. The most preferred concentration is about 4.5%.

It is necessary to carry out the reaction in a solvent which contains a carboxylic acid. Preferred solvents are carboxylic acids such as acetic acid, propionic acid, glutaric acid or a mixture of these acids. Mixtures of a carboxylic acid and a non-acidic solvent such as tolune, n-butyronitrile or dimethylacetamide may also be used. To facilitate product separation, a carboxylic acid solvent which has a higher boiling point than that of 3-pentenoic acid is preferred.

The reaction of the present invention may be carried out in a batch or continuous type process by heating under CO pressure a mixture of nickel(II) salt, hydrogen iodide, butadiene, and, preferably, water and a nitrogen or phosphine promoter in a carboxylic acid solvent The following are preferred operating conditions:

| | |
|---|---|
| Temperature | 90°C.–120° C. |
| CO pressure | 700 to 2000 psig |
| Solvent | Carboxylic Acid |
| Ni concentration | 0.5 to 1.0% by weight |
| Water concentration | 1.5 to 6.0% by weight |
| I/Ni | 5/1 to 10/1 |
| Promoter/Ni | 4/1 to 8/1 |

The invention is illustrated by the following examples, which are not intended to limit the scope of the invention.

EXAMPLES

Example 1

Carbonylation of Butadiene in Acetic Acid at 115° C. and 1000 psig with Ni/HI Catalyst Promoted by 2,6-Lutidine and Water.

A 120 mL mechanically stirred Hastelloy-C autoclave was charged with 5.0 g (16 mmole) of anhydrous Nickel iodide, 5.1 g (48 mmole) of 2,6-lutidine, 10.8 g 57% HI (48 mmoles HI; 258 mmoles $H_2O$), 1.0 g 1,2,4-trichlorobenzene (TCB, GC internal standard) and 82.6 g acetic acid solvent. The solution was heated to a temperature of 115° C. with agitation under an initial pressure of 750 psig carbon monoxide. The reaction was initiated by injecting a solution of 5.4 g (100 mmole) of butadiene and adjusting the total pressure to 1000 psig. Carbon monoxide was continuously fed to the autoclave from a reservoir so as to maintain the total pressure constant at 1000 psig. Samples were removed at intervals and analyzed on a 30 M J&W Scientific DBF-FAP capillary GC column for butadiene, crotyl derivatives, anhydrides, 3-pentenoic acid, 2-methyl-3-butenoic acid and valerolactone.

The GC analysis of the solutions indicated that crotyl iodide and its isomer 3-iodobutene-1, cis- and trans-crotyl acetate and 3-acetoxybutene-1 are rapidly formed initially and that these intermediates are more slowly converted to 3-pentenoic acid.

After 1 hour the butadiene (BD) conversion was 78.3%, the yield of cis- and trans-3-pentenoic acid (3PA) was 90.9%, the yield of 2-methyl-3-butenoic acid (2M3BA) was 4.2% and the yield of valerolactone (VL) was 5.0%. After 5 hours the BD conversion was 98.2%, the yield of 3PA was 74%, the yield of 2M3BA was 4.1% and the yield of valerolactone was 15.6%. The data indicate that 3PA is converted to valerolactone at high conversions.

The first order rate constant for the conversion of all C4 precursors (butadiene, butenyl iodides, butenyl esters) was 1.35 $Hr^{-1}$. The initial (first hour) 3PA formation rate, based on the linear initial 3PA concentration vs. time plot corresponds to a Space-Time-Yield (STY) of 946 mmoles 3PA/ L/Hr.

Example 2

Carbonylation of Butadiene in Anhydrous Acetic Acid at 115° C. and 1000 psig with Ni/HI Catalyst Promoted by 2,6-Lutidine.

The experiment in example 1 was repeated, except that the water was removed by adding an amount of acetic anhydride (10.8 g; 480 mmoles) equivalent to the water introduced with the aqueous HI. The reaction was allowed to run for a total of 5 hours. Samples were analyzed by GC as in Example 1. In addition, the less stable anhydrides of 3-pentenoic acid (3-pentenoic acetic mixed anhydride and bis-3-pentenoic anhydride) were analyzed by GC on a on a DB5 30 M J&W Scientific capillary GC column.

The GC analysis on the DB5 column indicated that 3-pentenoic acetic mixed anhydride and bis-3-pentenoic anhydride were formed at intermediate times and that these products were consumed as 3-pentenoic acid and acetic anhydride were formed. After 1 hour the butadiene conversion was 52.3% and the 3PA yield was 92.1%, the yield of 2M3BA was 3.2% and the yield of VL was 0.9%. After 5 hours the butadiene conversion was 86.3%, the 3PA yield was 88.3% and the VL yield was 6.8%. Analysis also showed that acetic anhydride concentration increased with time from an initial value of 0.7 mole % to 91.3 mole % after 4 hours.

The first order rate constant for the conversion of all C4 precursors (butadiene, butenyl iodides, butenyl esters) was 0.56 $Hr^{-1}$. The initial (first hour) 3PA formation rate, based on the linear initial 3PA concentration vs. time plot corresponds to a Space-Time-Yield (STY) of 569 mmoles 3PA/ L/Hr. The results indicate that water is not necessary for 3PA formation from butadiene but that the carbonylation is slower in the absence of water.

Example 3

Carbonylation of Butadiene in Anhydrous 3-Pentenoic acid at 115° C. and 1000 psig with Ni/$AlI_3$ Catalyst Promoted by 2,6-Lutidine.

The experiment in example 1 was repeated, except that the solvent was 3-pentenoic acid and the aqueous HI was replaced with an equivalent amount of anhydrous aluminum iodide (I/Ni=5). GC analysis on the DB5 column of a sample taken after 5 hours showed 53% butadiene conversion and bis-3-pentenoic anhydride (1.45 g; ca 14% yield) and crotyl pentenoates (0.34 g; 2.2% yield) as the major products.

Example 4

Carbonylation of Butadiene in Acetic Acid at 115° C. and 1000 psig with Ni/HI Catalyst Promoted by 2,6-Lutidine and Water: Lower Ni and HI Concentrations The experiment in Example 1 was repeated, except that the Nickel iodide concentration was reduced to 2.5 g (ca.

0.46% Ni in solution) and the HI concentration was reduced to maintain the same 5/1 iodide/Ni ratio as in Example 1. Additional water was added to maintain the water/butadiene ratio at 2.5/1. After 5 hours the butadiene conversion was 94%, the yield of 3PA was 90.5% and the yield of valerolactone was 3.5%. The first order rate constant for butadiene disappearance was 0.45 $Hr^{-1}$ and the initial STY was 407 mmoles 3PA/L/Hr. The data indicates that the reaction rate is reduced by more than a factor of 2 when the Ni and iodide concentrations are reduced by half.

Example 5
Carbonylation of Butadiene in Acetic Acid at 115° C. and 1000 psig with Ni/HI Catalyst Without Promoter.

The experiment in example 1 was repeated, except that the 2,6-lutidine was omitted. After 5 hours the butadiene conversion was 14.0%, the 3PA yield was 74.9% and the VL yield was 0.4%. The first order rate constant for butadiene disappearance was 0.02 $Hr^{-1}$ and the initial STY initial (first hour) space-time yield was 21 mmoles 3PA/L/Hr. The data indicate that a promoter is not necessary, but that the rate and 3PA yield are lower in the absence of a promoter.

Example 6
Carbonylation of Butadiene in Acetic Acid at 70° C. and 900 psig with Ni/HI Catalyst Without Promoter.

The experiment in example 5 was repeated, except that the temperature was reduced to 70° C., the CO pressure was 900 psig and the I/Ni ratio was increased to 10. After 5 hours the butadiene conversion was 23.1%, the 3PA yield was 84.1% and the initial space-time yield was 50 mmoles 3PA/L/Hr.

Example 7
Carbonylation of Butadiene using a Nickel Catalyst, an Iodide and 2,6-Lutidine Promoter at 100° C. and 900 psig using 10/1 I/Ni Ratio.

A 25 mL glass lined pressure vessel was charged with 5 mL of a solution containing approximately 3.7 g (68 mmol) butadiene, 14.4 g 57% aqueous HI (64 mmoles HI, 344 mmoles $H_2O$), 19.7 g (193 mmoles) acetic anhydride and 1.00 g 1,2,4-trichlorobenzene (internal GC standard) in 100 mL acetic acid. To this 5 mL aliquot was added 125 mg (0.4 mmol) of Nickel iodide and 257 mg (2.4 mmoles) 2,6-lutidine promoter. To remove entrapped air, the pressure vessel was pressurized with about 40 psig CO and then depressurized to atmospheric pressure. This procedure was repeated 3 times. The pressure vessel was then pressurized to 900 psig CO and heated to 100° C. with agitation for 4 hours. After 4 hours the heat was shut off, the pressure vessel was allowed to cool to room temperature and the excess gases were vented. The product was analyzed directly by GC on a DBFFAP 30 M J&W Scientific capillary GC column. The results are summarized in Table 1 below.

TABLE 1

| Compound | mmoles/100 BD Charged | Approx. Yield |
|---|---|---|
| Butadiene | 0.4 | — |
| s-Butyl acetate | 0.1 | 0.2 |
| s-Butyl iodide | 3.2 | 4.8 |
| Crotyl Iodides | 0.9 | — |
| Crotyl Acetates | 0.0 | |
| c/t 3PA | 54.9 | 82.4 |
| 2M3BA | 2.3 | 3.5 |
| VL | 3.9 | 5.9 |
| Total | 65.7 | (97% accounting) |

The conversion was 98% and the yield of 3PA+ valerolactone was 88.3%

Example 8–23

Carbonylation of Butadiene in Acetic Acid at 900 psig with Ni/HI in the Presence of Various Pyridine Type Base Promoters.

The experiment in Example 7 was repeated, except that the pyridine base, the temperature and the base to Ni ratio were varied. The reaction conditions were 1 M Butadiene, 10/1 HI/Ni, 0.47% Ni, 900 psig total pressure, 100 or 110° C. and 4 hour reaction time. The results are shown in Table 2.

TABLE 2

Butadiene Hydrocarboxylation with Nickel/HI/Pyridine Type Promoter

| Ex | Base/NI | Additive | Temp | Mmoles 3PA/ 100 BD | 3PA | 2M3BA | VL |
|---|---|---|---|---|---|---|---|
| 8 | 6 | Pyridine | 100 | 33.2 | 52.4 | 2.3 | 4.8 |
| 9 | 6 | 3,4-Lutidine | 110 | 48.2 | 61.6 | 3.2 | 9.5 |
| 10 | 4 | 2,6-Lutidine | 100 | 44.3 | 78.1 | 3.2 | 4.2 |
| 11 | 6 | 2,6-Lutidine | 100 | 55.2 | 85.9 | 3.6 | 3.8 |
| 12 | 6 | 2,6-Lutidine | 110 | 50.8 | 68.0 | 3.3 | 3.9 |
| 13 | 8 | 2,6-Lutidine | 110 | 53.1 | 65.5 | 2.8 | 2.0 |
| 14 | 6 | 2,6-Di-t-butylpyridine | 100 | 49.1 | 85.0 | 3.7 | 2.7 |
| 15 | 6 | 2,6-Diphenylpyridine | 100 | 47.5 | 70.5 | 3.2 | 10.1 |
| 16 | 6 | 3-Benzoylpyridine | 100 | 39.7 | 55.4 | 2.3 | 2.7 |
| 17 | 6 | 4-Benzoylpyridine | 100 | 38.6 | 55.3 | 2.3 | 2.6 |
| 18 | 6 | 3-Acetylpyridine | 100 | 37.2 | 52.0 | 2.1 | 1.7 |
| 19 | 6 | Isoquinoline | 100 | 19.5 | 51.6 | 1.7 | 10.0 |
| 20 | 6 | Quinaldine | 100 | 17.8 | 35.7 | 1.8 | 0.4 |
| 21 | 6 | 2-Fluoropyridine | 100 | 11.9 | 22.8 | 1.3 | 0.4 |

TABLE 2-continued

Butadiene Hydrocarboxylation with Nickel/HI/Pyridine Type Promoter

| Ex | Base/NI | Additive | Temp | Mmoles 3PA/ 100 BD | Yields 3PA | 2M3BA | VL |
|---|---|---|---|---|---|---|---|
| 22 | 8 | Polyvinylpyridine (2% cross-linked) (REILLEX(R) 402) | 100 | 9.9 | 26.9 | 1.0 | 0.0 |
| 23 | 4 | Isoquinoline | 100 | 4.0 | 16.1 | 0.0 | 5.1 |

Conditions: (1 M Butadiene, 10/1 HI/NI, 0.47% NI, 900 psi total Pressure, 4 Hour Reaction time)

Example 24–39

Carbonylation of Butadiene in Acetic Acid at 900 psig with Ni/HI in the Presence of Various Aromatic and Heterocyclic Nitrogen Base Promoters.

The experiment in Example 7 was repeated, except that the lutidine base was replaced with various aliphatic and aromatic nitrogen bases and the temperature and the base to Ni ratio were varied. The reaction conditions were 1 M butadiene, 10/1 HI/ Ni, 0.47% Ni, 900 psig total pressure, and 4 hour reaction time. The results are shown in Table 3.

Example 40–47

Carbonylation of Butadiene in Acetic Acid at 900 psig with Ni/HI in the Presence of Urea and Amide Promoters.

The experiment in Example 7 was repeated, except that the lutidine base was replaced with various urea and amide bases and the temperature and the base to Ni ratio were varied. The results are shown in Table 4.

TABLE 3

Butadiene Hydrocarboxylation with Nickel/HI With Aliphatic and Heterocyclic AmIne Promoters

| Ex | Class | Base/NI | Base | Temp | 3PA mmoles/ 100 BD | Yields 3PA | 2M3BA | VL |
|---|---|---|---|---|---|---|---|---|
| 24 | Tert-alkylamine | 6 | Triethylamine | 100 | 42.3 | 63.1 | 2.7 | 3.3 |
| 25 | Tert-Aralkyl Amine | 8 | Diphenylethylamine | 100 | 28.9 | 75.6 | 3.5 | 3.8 |
| 26 | Sec-alkylamine | 6 | Di-isopropylamine | 100 | 17.8 | 36.8 | 1.9 | 0.4 |
| 27 | Primary alkylamine | 6 | n-Butylamine | 100 | 32.2 | 58.8 | 2.5 | 1.6 |
| 28 | Primary alkylamine | 6 | tert-Butylamine | 100 | 5.6 | 16.3 | 1.5 | 0.0 |
| 29 | Imidazole | 6 | 1-Methylimidazole | 110 | 57.0 | 68.5 | 3.2 | 8.5 |
| 30 | Imidazole | 4 | 1-Methylimidazole | 110 | 37.8 | 57.7 | 2.8 | 3.7 |
| 31 | Imidazole | 6 | 4-Methylimidazole | 110 | 41.4 | 61.0 | 2.9 | 1.5 |
| 32 | Imidazole | 2 | 4-Methylimidazole | 110 | 12.7 | 29.7 | 1.7 | 0.6 |
| 33 | Imidazole | 6 | Imidazole | 100 | 55.5 | 71.7 | 2.7 | 3.6 |
| 34 | Heterocyc N Base | 6 | 2,4,5-Trimethylthiazole | 100 | 49.7 | 66.2 | 2.9 | 3.9 |
| 35 | Heterocyc N Base | 6 | Thiazole | 10 | 38.2 | 55.7 | 2.3 | 3.3 |
| 36 | Heterocyc N Base | 6 | 2,2,4-Trimethyl-2-oxazoline | 100 | 34.5 | 55.1 | 2.5 | 1.2 |
| 37 | Indole | 6 | 5-Methylindole | 100 | 9.8 | 16.8 | 1.0 | 0.4 |
| 38 | Indole | 6 | 1-Methylindole | 100 | 0.7 | 1.0 | 0.3 | 0.0 |
| 39 | Pyrazine | 6 | 2-Methylquinoxaline | 100 | 2.9 | 4.5 | 0.5 | 0.0 |

Conditions: (1 M Butadiene, 10/1 HI/NI, 0.47% NI, 900 psi total Pressure, 4 Hour Reaction time)

TABLE 4

Butadiene Hydrocarboxylation with Nickel/HI Using Urea and Amide Promoters

| Ex | Class | Base/NI | I/NI | Additive | Temp | 3PA mmoles/ 100 BD | Yields 3PA | 2M3BA | VL |
|---|---|---|---|---|---|---|---|---|---|
| 40 | Alkylurea | 12 | 10 | 1,1,3,3-Tetramethylurea | 110 | 58.8 | 69.9 | 2.9 | 1.7 |
| 41 | Alkylurea | 6 | 10 | 1,1,3,3-Tetramethylurea | 100 | 24.9 | 36.8 | 1.9 | 4.2 |
| 42 | thiourea | 6 | 10 | NN-Dibutylthiourea | 110 | 19.4 | 59.2 | 3.3 | 2.4 |
| 43 | thiourea | 4 | 10 | NN-Dibutylthiourea | 110 | 18.7 | 47.4 | 2.7 | 3.1 |

TABLE 4-continued

Butadiene Hydrocarboxylation with Nickel/HI Using Urea and Amide Promoters

| Ex | Base/ Class | NI | I/NI | Additive | Temp | 3PA mmoles/ 100 BD | Yields 3PA | 2M3BA | VL |
|---|---|---|---|---|---|---|---|---|---|
| 44 | thiourea | 12 | 10 | Thiourea | 110 | 4.7 | 5.6 | 0.0 | 0.0 |
| 45 | thiourea | 6 | 10 | Thiourea | 100 | 4.3 | 6.5 | 0.0 | 0.7 |
| 46 | Tert Amide | 12 | 10 | N,N-Dimethylacetamide | 100 | 21.6 | 47.9 | 2.2 | 0.0 |
| 47 | Tert Amide | 6 | 0 | Dimethylformamide | 100 | 8.2 | 22.5 | 1.4 | 0.4 |

Conditions: (1 M Butadiene, 10/1 HI/NI, 0.47% NI, 900 psi total Pressure, 4 Hour Reaction time)

Example 48–51

Carbonylation of Butadiene in Acetic Acid at 900 psig with Ni/HI in the Presence of a Quaternary Ammonium or Phosphonium Iodide Promoter.

The experiment in Example 7 was repeated, except that the lutidine base was replaced with a quaternary ammonium or phosphonium iodide and the temperature and the base to Ni ratio were varied. The results are shown in Table 5.

TABLE 5

Butadiene Hydrocarboxylation with Nickel/HI and Quaternary Ammonium and Phosphonium Iodide Promoters

| Ex | Base/ Class | NI | I/NI | Additive | Temp | 3PA mmoles/ 100 BD | Yields 3PA | 2M3BA | VL |
|---|---|---|---|---|---|---|---|---|---|
| 48 | Quat Amm Salt | 4 | 4 | Bu₄NI | 100 | 32.7 | 49.3 | 2.4 | 6.6 |
| 49 | Quat Amm Salt | 6 | 4 | Bu₄NI | 100 | 28.0 | 41.7 | 2.0 | 7.1 |
| 50 | Quat Amm Salt | 8 | 2 | Bu₄NI | 100 | 23.0 | 60.0 | 3.2 | 7.2 |
| 51 | Quat Phos Salt | 3 | 7 | MePh₃PI* | 115 | 20.4 | 26.9 | 1.9 | 9.9 |

Conditions: (1M Butadiene, 0.47% Ni, 900 psi total Pressure, 4 Hour Reaction time) Run at 115° C. and 1000 psi CO

Example 52

Carbonylation of Butadiene in Acetic Acid at 90° C. and 900 psig With Triphenylphosphine Promoter.

A 120 mL mechanically stirred Hastelloy-C autoclave was charged with a solution of 2.0 g (8 mmole) of Nickel acetate, 8.4 g (32 mmole) of triphenylphosphine, 9.0 g 57% HI (20 mmoles HI; 215 mmoles $H_2O$), 1.5 g (85 mmoles) water and 1.0 g 1,2,4-trichlorobenzene (TCB, GC internal standard) in 84 g acetic acid solvent (total volume approximately 100 mL). The solution was heated to a temperature of 90° C. under an initial pressure of 700 psig of carbon monoxide. The reaction was initiated by injecting 5.4 g (100 mmole) of butadiene and adjusting the total pressure to 900 psig with CO. Carbon monoxide was continuously fed to the autoclave from a reservoir so as to maintain the total pressure constant at 900 psig. Liquid samples were removed at intervals for GC analysis on a DBFFAP 30 M J&W Scientific capillary GC column. The reaction was allowed to run for a total of 3 hours.

The product was a clear yellow homogeneous solution from which some crotyltriphenylphosphonium iodide crystallized on standing.

The following results were obtained from the GC analyses of the sample taken after 3 hours:

| Product | moles (per mmoles BD charged) |
|---|---|
| Butadiene | 0.5 |
| Mixed Butenes | 4.6 |
| 3-Acetoxybutene-1 | 0.0 |
| Crotyl Acetate | 0.8 |
| cis + trans 3-pentenoic acid | 72.2 |
| 2-Methyl-3-butenoic acid | 2.5 |
| Valerolactone | 1.9 |

The butadiene conversion after 3 hours was 99%, the yield of 3-pentenoic acid was 72.6%, and the yield of valerolactone was 1.8%. The first order rate constant for the conversion of butadiene was 1.3 $Hr^{-1}$, corresponding to a turnover frequency of 17 moles butadiene converted per g-atom of Nickel per hour.

Example 53

Carbonylation of Butadiene in Acetic Acid at 90° C. and 900 psig With Triphenylphosphine Promoter: Lower Ni and HI and Promoter Concentrations.

The experiment in example 52 was repeated, except that the nickel concentration was reduced to 4 mmoles/100 mL. The Ni/HI/Ph₃P ratio was maintained at 1/5/4. After 3 hours the butadiene conversion was 88%, the yield of 3-pentenoic acid was 85%, and the yield of valerolactone was 1.5%. The first order rate constant for butadiene conversion was 0.29 $Hr^{-1}$, corresponding to a turnover frequency of 5.3 moles butadiene converted per g-atom of Ni per hour.

Example 54
Carbonylation of Butadiene in Acetic Acid at 80° C. and 900 psig With Triphenylphosphine Promoter: Lower Temperature.

The experiment in example 52 was repeated, except that the butadiene (4.0 g) was added over 60 minutes and the temperature was 80° C. Analysis of a sample taken 60 minutes after completion of the butadiene addition showed 88% butadiene conversion, 5.4% butenyl acetates, 73% cis-and trans-3-pentenoic acid, 1.9% 2-methyl-3-butenoic acid and 2.7% valerolactone. Considering the butadiene and butenyl esters as equivalent feeds, the yield of 3-pentenoic acid is 89%. When the reaction is allowed to run for longer periods the yield of 3PA decreases.

Example 55
Carbonylation of Butadiene using a Nickel Catalyst, an Iodide Promoter and Triphenylphosphine Ligand.

A 25 mL glass lined pressure vessel was charged with 5 mL of a solution containing 3.4 g (63 mmol) butadiene, 1.00 g (4.0 mmol) of Nickel acetate tetrahydrate, 3.6 g (200 mmole) water and 1.00 g 1,2,4-trichlorobenzene (internal GC standard) in 100 mL acetic acid. To this 5 mL aliquot was added 1 mL (1.0 mmole) of a 1 Molar solution of HI in acetic acid and 0.210 g (0.8 mmole) Triphenylphosphine. To remove entrapped air, the pressure vessel was pressurized with about 40 psig CO and then depressurized to atmospheric pressure. This procedure was repeated 3 times. Some butadiene was lost during this procedure. The vessel was then pressurized to 900 psig CO and heated to 90° C. with agitation for 4 hours. After 4 hours the heat was shut off, the pressure vessel was allowed to cool to room temperature and the excess gases were vented. The product was analyzed directly by GC on a DBFFAP 30 M J&W Scientific capillary GC column. The results are summarized in Table 6.

Examples 56–60
Carbonylation of Butadiene using a Nickel Catalyst, an Iodide Promoter and Triphenylphosphine Ligand.

The experiment in Example 55 was repeated, except that iodide promoter and the reaction temperature were varied. The results are shown in Table 6.

TABLE 6

Butadiene Carbonylation with Nickel/Iodide Using Phosphine Promoters

| Ex | Temp | Iodide | Mole % Cr-X* | Mole % 3PA |
|---|---|---|---|---|
| 55 | 90  | HI   | 12.8 | 24.9 |
| 56 | 90  | AlI$_3$ | 9.0  | 12.6 |
| 57 | 90  | BI$_3$  | 6.9  | 30.0 |
| 58 | 110 | HI   | 12.8 | 25.2 |
| 59 | 110 | CrI$_3$ | 15.3 | 14.0 |
| 60 | 110 | SnI$_4$ | 2.2  | 6.4  |

*Cr-X = Crotyl intermediates (Mixture of 3-acetoxybutene-1, crotyl acetate and crotyl iodides)
Conditions: About 1 M Butadiene, 0.23% Ni as Ni(OAc)$_2$.4H$_2$O, 3.6% H$_2$O in acetic acid, 5/1 I/NI, 4/1 Ph$_3$P/Ni, 900 psi total Pressure, 4 Hour Reaction time

Examples 61–63
Carbonylation of Butadiene using a Nickel Catalyst, an Iodide Promoter and Various Phosphine Ligands.

The experiment in Example 55 was repeated, except that the phosphine ligand was varied. The results are shown in Table 7.

TABLE 7

Butadiene Carbonylation with Nickel/Iodide Using Phosphine Promoters

| Ex | Temp | Ligand | Mole % Cr-X* | Mole % 3PA |
|---|---|---|---|---|
| 61 | 110 | C$_2$H$_5$PPh$_2$ | 13.9 | 69.7 |
| 62 | 110 | DPPB | 8.1 | 76.3 |
| 63 | 110 | (p-MeOC$_6$H$_4$)$_3$P | 2.3 | 78.7 |

DPPB = 1,4-bis(diphenylphosphino) butane
*Cr-X = Crotyl intermediates (Mixture of 3-acetoxybutene-1, Crotyl acetate and crotyl iodides)
Conditions: About 0.76 M Butadiene, 0.23% Ni as Ni(OAc)$_2$.4H$_2$O, 3.6% H$_2$O in acetic acid, 5/1 I/NI, 4/1 Ph$_3$P/Ni, 900 psi total Pressure, 4 Hour Reaction time

Examples 64–69
Carbonylation of Butadiene at High Pressures using a Nickel/HI Catalyst and as Promoter.

The experiment in Example 7 was repeated, except that the temperature and CO pressure were varied, lutidine/Ni mole ratio was 4, and the Ni concentration was 0.94%. The water concentration was also reduced by adding acetic anhydride (54.6 g/100 mL). The results are shown in Table 8.

TABLE 8

Butadiene Carbonylation With NI/HI/Promoter Under High CO Pressure Conditions

| Ex | Temp | Press (Total) | Iodide | Promoter | Prom/Ni | 3PA mole % | VL mole % |
|---|---|---|---|---|---|---|---|
| 64 | 120 | 2000 | HI | None | 0 | 0.6 | 0.7 |
| 65 | 120 | 2000 | HI | Ph$_3$P | 4 | 10.8 | 4.4 |
| 66 | 120 | 2000 | CrI$_3$ | Mo(CO)$_6$ | 8 | 15.1 | 5.8 |
| 67 | 120 | 3500 | HI | None | 0 | 1.1 | 0.7 |
| 68 | 120 | 3500 | HI | Ph$_3$P | 4 | 10.8 | 1.4 |
| 69 | 120 | 3500 | CrI$_3$ | Mo(CO)$_6$ | 8 | 16.3 | 5.0 |

Conditions: About 0.9 M Butadiene, 0.47% Ni as Ni(OAc)$_2$.4H$_2$O, 3.6% H$_2$O in acetic acid, 5/1 I/NI, 4/1 Ph$_3$P/Ni, 900 psi total Pressure, 4 Hour Reaction time

Example 70
Carbonylation of Butadiene in Acetic Acid at 100° C. and 900 psi with Ni/HI Catalyst Promoted by Molybdenum Hexacarbonyl.

The experiment in Example 1 was repeated, except that the catalyst was nickel acetate (2.0 g; 8 mmole), the amount of 57% aqueous HI was 9.0 g (40 mmols HI+2.15 mmoles H$_2$O), and the lutidine promoter was replaced with molybdenum hexacarbonyl (8.4 g; 32 mmoles). The carbonylation was run at 100° C. and 900 psi CO. After 3 hours the butadiene and crotyl intermediate conversion was 32%, and the yield of 3PA was 49.1%.

What is claimed is:

1. A process for making 3-pentenoic acid which comprises (1)reacting butadiene with carbon monoxide in the presence of nickel and an iodide source selected from the group consisting of HI and iodides of metals selected from the group consisting of B, Al, Ga, Sc, Y, La, Ce, Pr, Nd, Sm, Eu, Gd, Tb, Dy, Ho, Er, Yb, Lu, Ge, Sn, Ti, Zr, Cr, Mo, W, Mn, Fe, Co, Ni and Zn in a carboxylic acid-containing solvent at a temperature between about 60° C. and about 140° C. and a pressure between about 200 psig and about 4000 psig and (2) recovering 3-pentenoic acid.

2. The process of claim 1 in which the butadiene and carbon monoxide are reacted in the presence of water.

3. The process of claim 2 in which the butadiene and carbon monoxide are reacted in the presence of a promoter selected from the group consisting of trialkylamine, wherein each alkyl contains from 1 to 5 carbon atoms, or a hydrogen iodide or quartenary ammonium iodide salt thereof;

arylalkylamine, wherein each aryl group contains from 6 to 20 carbon atoms and each alkyl contains from 1 to 5 carbon atoms, or a hydrogen iodide or quartenary ammonium iodide salt thereof;

triarylamine, wherein each aryl group contains from 6 to 20 carbon atoms, or a hydrogen iodide or quartenary ammonium iodide salt thereof;

pyridine, optionally $C_1$–$C_5$ alkyl- or $C_6$–$C_{20}$ aryl-substituted, or a hydrogen iodide or quartenary ammonium iodide salt thereof;

quinoline, optionally $C_1$–$C_5$ alkyl- or $C_6$–$C_{20}$ aryl-substituted, or a hydrogen iodide or quartenary ammonium iodide salt thereof;

isoquinoline, optionally $C_1$–$C_5$ alkyl- or $C_6$–$C_{20}$ aryl-substituted, or a hydrogen iodide or quartenary ammonium iodide salt thereof;

imidazole, optionally $C_1$–$C_5$ alkyl- or $C_6$–$C_{20}$ aryl-substituted, or a hydrogen iodide or quartenary ammonium iodide salt thereof;

thiazole, optionally $C_1$–$C_5$ alkyl- or $C_6$–$C_{20}$ aryl-substituted, or a hydrogen iodide or quartenary ammonium iodide salt thereof;

oxazole, optionally $C_1$–$C_5$ alkyl- or $C_6$–$C_{20}$ aryl-substituted, or a hydrogen iodide or quartenary ammonium iodide salt thereof;

$C_1$–$C_5$ alkyl-substituted urea or thiourea; aliphatic amide;

trialkylphosphine, wherein each alkyl contains from 1 to 5 carbon atoms;

triarylphosphine, wherein each aryl group contains from 6 to 20 carbon atoms;

dialkylarylphosphine, wherein the aryl group contains from 6 to 20 carbon atoms and each alkyl contains from 1 to 5 carbon atoms;

alkyldiarylphosphine, wherein each aryl group contains from 6 to 20 carbon atoms and the alkyl contains from 1 to 5 carbon atoms; and bidentate phosphine of the formula $R^3{}_2P\text{-}Q\text{-}PR^4{}_2$ in which Q is a 3 to 6 carbon atom bridging group and $R^3$ and $R^4$ are the same or different $C_1$–$C_{10}$ alkyl or $C_6$–$C_{20}$ aryl groups; and compounds of Group VI metals of the Periodic Table.

4. The process of claim 3 in which, the iodide is HI, the temperature is in the range of 100° C. to 120° C., the CO pressure is in the range of 900 psig to 1800 psig, and the solvent is a monocarboxylic acid or a dicarboxylic acid containing 1 to 10 carbon atoms.

5. The process of claim 4 in which the nickel is in the form of a Ni(II) salt.

6. The process of claim 5 where the promoter is selected from the group consisting of molybdenum hexacarbonyl, molybdenum (II) acetate dimer, and molybdenum (III) halide, where the halide is chlorine, bromide, or iodide.

* * * * *